United States Patent [19]
Maggioni et al.

[11] Patent Number: 4,599,461
[45] Date of Patent: Jul. 8, 1986

[54] PROCESS FOR THE SYNTHESIS OF O-ISOPROPOXYPHENOL

[75] Inventors: Paolo Maggioni, Montevecchia; Francesco Minisci, Milan; Mariano Correale, Bonate Sotto, all of Italy

[73] Assignee: Brichima Spa, Milano, Italy

[21] Appl. No.: 690,120

[22] Filed: Jan. 10, 1985

[30] Foreign Application Priority Data

Jan. 20, 1984 [IT] Italy ................. 19249 A/84

[51] Int. Cl.⁴ ............................................. C07C 41/16
[52] U.S. Cl. ................................................ 568/652
[58] Field of Search ........................................ 568/652

[56] References Cited

U.S. PATENT DOCUMENTS 3,927,118 12/1975 Ozretich ........................ 568/652
4,252,985 2/1981 Rakoutz ........................ 568/652
4,263,462 4/1981 Michelet et al. ................ 568/652

FOREIGN PATENT DOCUMENTS 0053633 5/1981 Japan ........................... 568/652

Primary Examiner—Bernard Helfin

Attorney, Agent, or Firm—Stevens, Davis, Miller & Mosher

[57] ABSTRACT

A process for preparing o-isopropoxyphenol (I) by means of the reaction:

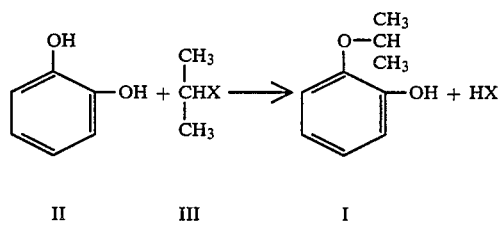

II  III  I in which X is a halogen atom and in which the pyrocatechol (II) is reacted with the isopropyl halide (III) in the presence of an alkaline base in the solid state and of a solid-liquid phase transfer catalyst, in a reaction medium constituted by one or more organic solvents.

The catalyst is constituted by a quaternary ammonium or phosphonium salt.

The reaction is conducted in a nitrogen atmosphere, at atmospheric pressure, under agitation, at a temperature of preferably between 50° C. and 130° C.

2 Claims, No Drawings

PROCESS FOR THE SYNTHESIS OF O-ISOPROPOXYPHENOL

This invention relates to a new process for the synthesis of o-isopropoxyphenol (I), based on the reaction between pyrocatechol (II) and an isopropyl halide (III), in accordance with reaction (1):

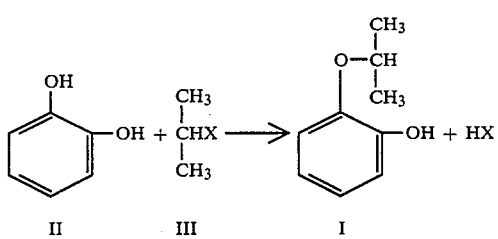

in which X is a halogen atom.

More particularly, the invention relates to a process for the synthesis of isopropoxyphenol (I) by reacting pyrocatechol (II) with an isopropyl halide (III) in the presence of an alkaline base and a solid-liquid phase transfer catalyst in a reaction medium constituted by one or more organic solvents.

O-isopropoxyphenol is an intermediate of considerable interest in the production of large-consumption insecticides.

The processes used for preparing o-isopropoxyphenol according to the known art are based on the reaction between an alkaline pyrocatechol salt (IV) and an isopropyl halide, as represented in reaction (2):

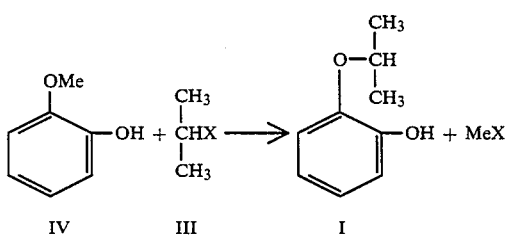

in which Me is an alkaline metal atom and X is a halogen atom.

These processes have various drawbacks. Firstly the reaction rate is rather low at the boiling point of isopropyl halides, because of which it is necessary to operate under pressure in order to increase the reaction temperature and thus the reaction rate. Furthermore, in all cases the complete conversion of the alkaline pyrocatechol salt requires a considerable time and the use of an excess of isopropyl halide, and leads to a large quantity of by-products such as pyrocatechol diether and nuclear alkylation products.

We have now discovered a new process which enables these drawbacks to be obviated or reduced, to obtain o-isopropoxyphenol with a high reaction rate and high selectivity, and thus in a manner more economical than with known processes.

The process according to the present invention is characterised in that reaction (1) for obtaining the o-isopropoxyphenol (I) is conducted by treating the pyrocatechol (II) with isopropyl halide (III) in the presence of a solid-liquid phase transfer catalyst.

More particularly, the process according to the present invention is characterised in that the reaction between pyrocatechol and isopropyl halide is conducted in the presence of a catalyst constituted by a quaternary ammonium or quaternary phosphonium salt, and of an alkaline base in the finely pulverised solid state.

The process according to the present invention is further characterised in that the reaction between pyrocatechol and isopropyl halide is conducted in a reaction medium which can be constituted by many types of organic solvents or their mixtures.

The isopropyl halide used is preferably isopropyl bromide, the alkaline base used is preferably sodium or potassium carbonate or sodium or potassium hydroxide, and the reaction medium can consist of any of those solvents in which the pyrocatechol, the isopropyl halide and the catalyst have sufficient solubility at the reaction temperature.

In this respect, the reaction medium can consist of solvents such as hydrocarbons (for example n.heptane, cyclohexane, decalin, toluene, xylene etc.), alcohols (for example butyl, hexyl, allyl alcohols etc.), ethers (for example $C_6$–$C_{12}$ aliphatic ethers, arylalkyl ethers, diaryl ethers, cyclic ethers etc.), ketones (for example $C_6$–$C_{12}$ aliphatic ketones, alkylaryl ketones, cyclic ketones etc.), aliphatic or aromatic nitriles, or other types of organic compounds.

In addition, mixtures of solvents of very different polarities can also be used, and this constitutes a further characteristic of the process of the present invention.

These mixtures are particularly advantageous in carrying out product separation at the end of the reaction; in particular, separation of the unreacted pyrocatechol and catalyst is very simple if operating with a high-boiling solvent in which the pyrocatechol and catalyst are poorly soluble at ambient temperature (for example a hydrocarbon solvent), in mixture with a low-boiling polar solvent (for example an alcohol) which allows the pyrocatechol and catalyst to dissolve. By operating with such a system, the low-boiling solvent can be removed at the end of the reaction by distillation, and the distillation residue is then constituted by two phases which can be separated at ambient temperature. The lower phase contains the catalyst and unreacted pyrocatechol with a small quantity of o-isopropoxyphenol, and when separated can be recycled directly to a subsequent preparation. The upper phase is constituted by the solution of o-isopropoxyphenol, which can be recovered by distillation.

The quaternary ammonium and phosphonium salts used as catalysts have the following general formulas:

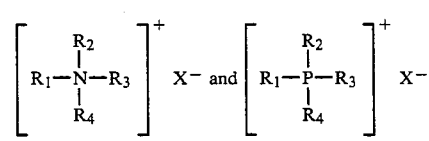

in which $R_1$, $R_2$, $R_3$ and $R_4$ are equal or different hydrocarbon groups of between 1 and 18 carbon atoms, possibly substituted, and X⁻ is preferably a hydrogen halide ion.

The reaction between pyrocatechol and isopropyl halide according to the present invention is conducted in a nitrogen atmosphere at atmospheric pressure under agitation, at a temperature preferably of between 50° C. and 130° C. The molar ratio of pyrocatechol to alkaline base is preferably between 2.5 and 0.5, and the molar ratio of pyrocatechol to isopropyl alcohol is preferably between 0.8 and 1.6. The quantity of catalyst used in the reaction is preferably between 0.01 and 0.5 moles per equivalent of alkaline base.

The following non-limiting examples are given to illustrate the process according to the present invention.

EXAMPLE 1

A solvent mixture constituted by 240 ml of isobutyl alcohol and 560 ml of decalin is fed into a reactor of 2000 ml capacity, and 110 g (1 mole) of pyrocatechol, 123 g (1 mole) of isopropyl bromide, 58 g (0.55 moles) of sodium carbonate, 1.6 g of sodium hydrosulphite, and 46 g (0.1427 moles) of tetrabutylammonium bromide as catalyst, are added.

The reaction is effected in a nitrogen atmosphere at atmospheric pressure under energetic agitation at a temperature of 90° C. for 15 hours.

The reaction mixture is then cooled to ambient temperature, the inorganic salts are separated by filtration, and the filtrate is distilled under reduced pressure in order to recover the isobutyl alcohol and unreacted isopropyl bromide, and these can be recycled to a subsequent preparation.

The distillation residue consists of two phases which are separated at ambient temperature.

On gas chromatography analysis, the lower phase (117.29 g) shows the following composition: decalin 8.36%; o-isopropoxyphenol 15.79%; pyrocatechol 39.07%; tetrabutylammonium bromide and other products 36.78%. This solution can be recycled as such to a subsequent preparation.

On gas chromatography analysis, the upper phase (533.40 g) is found to consist of 12.23% of o-isopropoxyphenol, and is distilled with rectification to obtain o-isopropoxyphenol, the separated solvent consisting essentially of decalin, and this can be recycled.

The pyrocatechol conversion is 58.38%, with a o-isopropoxyphenol molar yield of 94.38%.

EXAMPLE 2

This example was carried out in the same manner as Example 1, but with the difference that only isobutyl alcohol (800 ml) was used as the reaction solvent.

After cooling the reaction mixture, 560 ml of decalin were added, the inorganic salts were separated by filtration, and the filtrate was distilled under reduced pressure to recover the isobutyl alcohol and unreacted isopropyl bromide.

The distillation residue was constituted by two phases which were separated at ambient temperature.

The lower phase (126.97 g) had the following composition: decalin 8.36%; o-isopropoxyphenol 13.77%; pyrocatechol 40.51%; tetrabutylammonium bromide and other products 37.36%.

The upper phase (509.35 g) which contained 11.73% of o-isopropoxyphenol, was distilled with rectification to obtain o-isopropoxyphenol and separate the decalin.

The pyrocatechol conversion was 53.29%, with a o-isopropoxyphenol molar yield of 95.35%.

EXAMPLE 3

This example was carried out substantially in a manner analogous to the preceding examples, but with the difference that in this example the reaction was effected without the use of a catalyst and with a different solvent.

8.4 g (0.0763 moles) of pyrocatechol, 9.38 g (0.0763 moles) of isopropyl bromide, 4.44 g (0.0419 moles) of sodium carbonate, 0.13 g of sodium hydrosulphite and, as reaction solvent, 61.2 ml of methyl isobutylketone, are fed into a reactor of 100 ml capacity.

The reaction is carried out in a nitrogen atmosphere at atmospheric pressure under energetic agitation at a temperature of 90° C. as in the preceding examples, for 5 hours.

On gas chromatography analysis the reaction mixture was found to have the following composition: o-isopropoxyphenol 5.56%; pyrocatechol 93.69%; other products 0.75%.

EXAMPLES 4, 5 AND 6

These examples were carried out in the same manner as Example 3, and in particular without the use of a catalyst, but using reaction solvents different from those of Example 3, as shown in the following table, which also gives the results of the gas chromatography analysis of the reaction mixture.

TABLE

| | | Reaction mixture composition | | |
|---|---|---|---|---|
| Ex. No. | Reaction solvent | o-isopropoxy-phenol % | pyrocatechol % | others % |
| 4 | Chlorobenzene (61.2 ml) | 0.89 | 97.60 | 1.51 |
| 5 | Anisole (61.2 ml) | 0.78 | 98.86 | 0.36 |
| 6 | Nitrobenzene (61.2 ml) | 11.85 | 87.42 | 0.73 |

EXAMPLE 7

Example 7 was carried out in the same manner as Example 3, but with the difference that in Example 7 the reaction was effected in the presence of a catalyst, namely 3.57 g (0.0111 moles) of tetrabutylammonium bromide, which was fed together with the substances fed in Example 3.

On gas chromatography analysis, the reaction mixture was found to have the following composition: o-isopropoxyphenol 48.17%; pyrocatechol 50.60%; other products 1.23%.

A comparison of these results with those of Example 3 emphasises the fundamental importance of the catalsyt in converting pyrocatechol into o-isopropoxyphenol.

EXAMPLES 8, 9 AND 10

These examples were carried out in the manner of Example 7, and in particular the reaction was conducted in the presence of a catalyst, but with the difference that the solvents used in the reaction were those of Examples 4, 5 and 6 respectively, as shown in the following table which also gives the analytical results of the reaction mixture.

TABLE

| Ex. No. | Reaction solvent | Reaction mixture composition | | |
|---|---|---|---|---|
| | | o-isopropoxy-phenol % | pyrocatechol % | others % |
| 8 | Chlorobenzene (61.2 ml) | 31.51 | 62.85 | 5.64 |
| 9 | Anisole (61.2 ml) | 55.60 | 40.84 | 3.56 |
| 10 | Nitrobenzene | 59.74 | 32.10 | 8.16 |

The fundamental role of the catalyst and the influence of the type of solvent on the reaction between pyrocatechol and isopropyl bromide are clear from an examination of the results of these examples and their comparison with the results of Examples 4, 5 and 6 respectively.

We claim:

1. A process for preparing o-isopropoxyphenol (I) by means of the reaction:

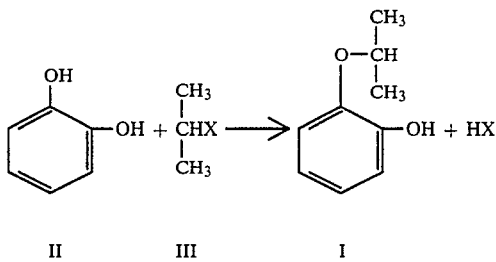

in which X is a halogen atom, in a reaction medium constituted by a mixture of organic solvents, of pyrocatechol (II) with an isopropyl halide (III), in the presence of an alkaline base in the solid state and of a solid-liquid phase transfer catalyst comprising a quaternary ammonium salt of general formula:

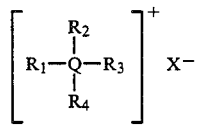

in which $R_1$, $R_2$, $R_3$ and $R_4$ are equal or different unsubstituted or substituted hydrocarbon groups containing between 1 and 18 carbon atoms, Q is nitrogen or phosphorus and $X^-$ is a monovalent anion, and wherein:
   (a) the alkaline base is sodium or potassium carbonate or sodium or potassium hydroxide;
   (b) said mixture of organic solvents comprises one solvent which is a low boiling alcohol, and one which is a high-boiling hydrocarbon;
   (c) the molar ratio of pyrocatechol to isopropyl halide is between 0.8 and 1.6;
   (d) the molar ratio of pyrocatechol to alkaline base lies between 2.5 and 0.5;
   (e) the quantity of catalyst used lies between 0.01 and 0.5 moles per equivalent of alkaline base; and
   (f) the reaction is conducted in a nitrogen atmosphere, at atmospheric pressure, under agitation, at a temperature between 50° and 130° C.

2. A process as claimed in claim 1, wherein the isopropyl halide used is preferably isopropyl bromide.

* * * * *